US00PP35949P2

(12) United States Plant Patent
Hofmann

(10) Patent No.: US PP35,949 P2
(45) Date of Patent: Jul. 2, 2024

(54) ***PETUNIA* PLANT NAMED 'INPETBEACH'**

(50) Latin Name: ***Petunia* X *hybrida***
Varietal Denomination: INPETBEACH

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 18/376,236

(22) Filed: Oct. 3, 2023

(51) Int. Cl.
*A01H 5/02* (2018.01)
*A01H 6/82* (2018.01)

(52) U.S. Cl.
USPC ..... Plt./356.23

(58) Field of Classification Search
USPC ..... Plt./356.1, 356.23
See application file for complete search history.

*Primary Examiner* — Susan McCormick Ewoldt
(74) *Attorney, Agent, or Firm* — C. Anne Whealy

(57) ABSTRACT

A new and distinct *Petunia* plant named 'INPETBEACH', characterized by its upright to outwardly spreading and mounding plant habit; vigorous growth habit and rapid growth rate; freely branching habit; dense and bushy plant form; early and freely flowering habit; large single-type flowers that are bright purplish pink in color with white-colored throats; and excellent container and garden performance.

2 Drawing Sheets

Figure 1:
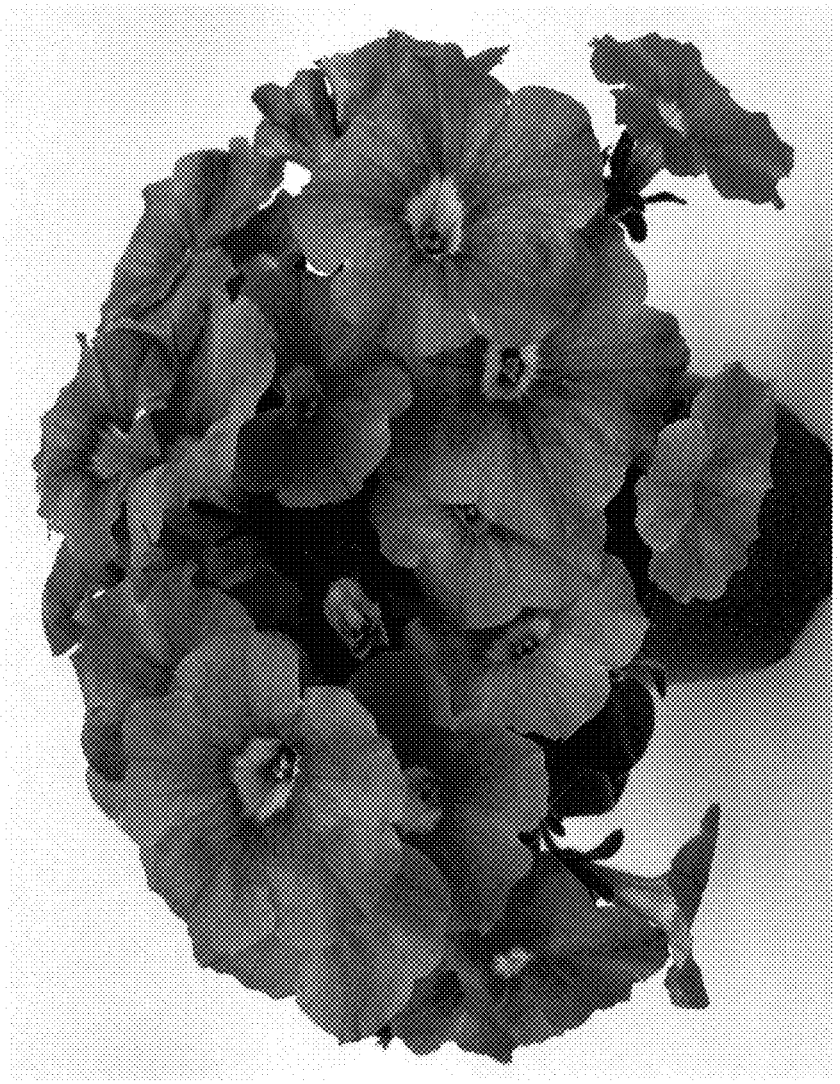

Botanical designation: *Petunia* X *hybrida.*
Cultivar denomination: 'INPETBEACH'.

BACKGROUND OF THE INVENTION

The present invention relates to a new and distinct cultivar of *Petunia* plant, botanically known as *Petunia* X *hybrida* and hereinafter referred to by the name 'INPETBEACH'.

The new *Petunia* plant is a product of a planned breeding program conducted by the Inventor in Heidesheim and Gensingen, Germany. The objective of the breeding program is to create new vigorous, freely-branching and uniformly mounding *Petunia* plants with early and freely flowering habit, attractive flowers and good garden performance.

The new *Petunia* plant originated from a cross-pollination made by the Inventor in June, 2019 in Heidesheim, Germany of a proprietary selection of *Petunia* X *hybrida* identified as code number pt18-4122-5, not patented, as the female, or seed, parent with *Petunia* X *hybrida* 'Kerversalm', disclosed in U.S. Plant Pat. No. 19,329, as the male, or pollen, parent. The new *Petunia* plant was discovered and selected by the Inventor as a single flowering plant within the progeny of the stated cross-pollination in a controlled greenhouse environment in Gensingen, Germany in May, 2022.

Asexual reproduction of the new *Petunia* plant by vegetative terminal cuttings in a controlled greenhouse environment in Gensingen, Germany since May, 2022 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INPETBEACH'. These characteristics in combination distinguish 'INPETBEACH' as a new and distinct *Petunia* plant:

1. Upright to outwardly spreading and mounding plant habit.
2. Vigorous growth habit and rapid growth rate.
3. Freely branching habit; dense and bushy plant form.
4. Early and freely flowering habit.
5. Large single-type flowers that are bright purplish pink in color with white-colored throats.
6. Excellent container and garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are denser than and not as open as plants of the female parent selection.
2. Plants of the new *Petunia* have larger and smoother flowers than plants of the female parent selection.
3. Flowers of plants of the new *Petunia* are purplish pink in color with white-colored throats whereas flowers of plants of the female parent selection are purplish pink in color with purplish pink-colored throats.

Plants of the new *Petunia* can be compared to plants of the male parent, 'Kerversalm'. In side-by-side comparisons, plants of the new *Petunia* differ primarily from plants of 'Kerversalm' in the following characteristics:

1. Plants of the new *Petunia* are larger and more outwardly spreading than plants of 'Kerversalm'.
2. Flowers of plants of the new *Petunia* are bright purplish pink in color whereas flowers of plants of 'Kerversalm' are duller purplish pink in color.

Plants of the new *Petunia* can be compared to plants of *Petunia* X *hybrida* 'Veranda Salmon', not patented. In side-by-side comparisons, plants of the new *Petunia* differ primarily from plants of 'Veranda Salmon' in the following characteristics:

1. Plants of the new *Petunia* are larger and more outwardly spreading than plants of 'Veranda Salmon'.
2. Leaves of plants of the new *Petunia* are darker green in color than leaves of plants of 'Veranda Salmon'.
3. Flowers of plants of the new *Petunia* are bright purplish pink in color whereas flowers of plants of 'Veranda Salmon' are duller purplish pink in color.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'INPETBEACH' grown in a container.

Figure 2:
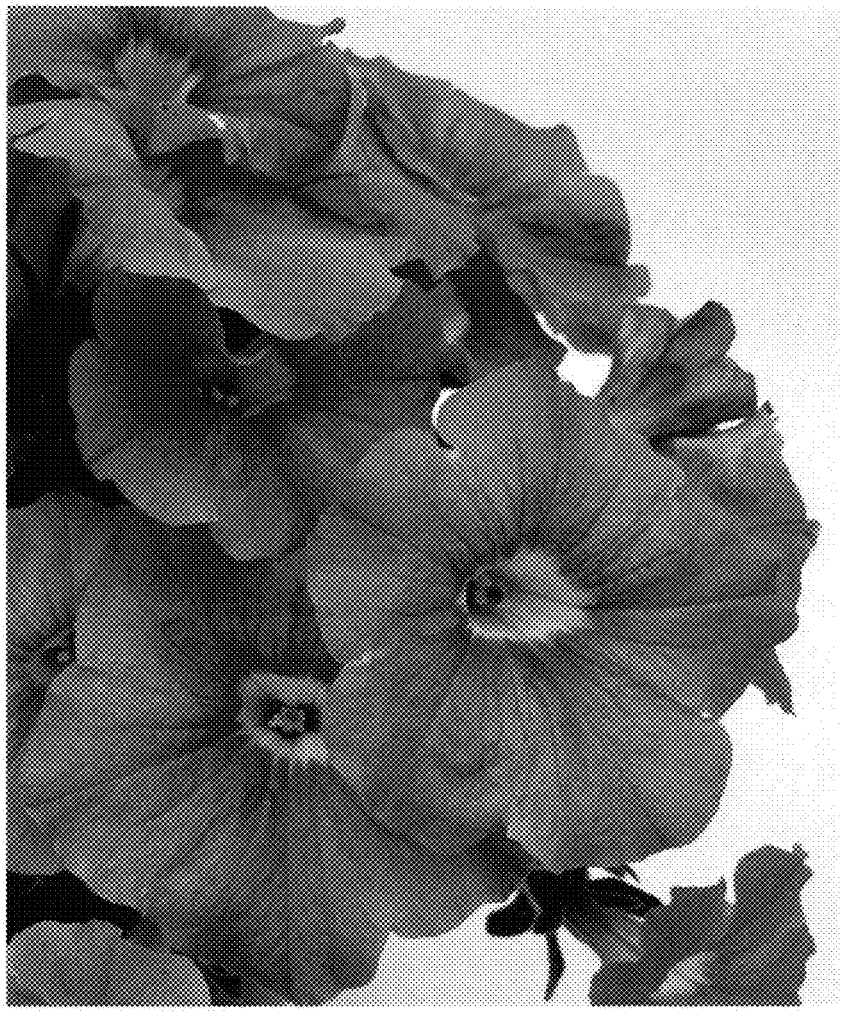

The photograph on the second sheet (FIG. 2) is a close-up view of a typical flowering plant of 'INPETBEACH'.

DETAILED BOTANICAL DESCRIPTION

The aforementioned photographs and following observations and measurements describe plants grown during the late spring in 10-cm containers in a glass-covered greenhouse in Loudon, New Hampshire and under cultural practices typical of commercial *Petunia* production. During the production of the plants, day and night temperatures averaged 20 C. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'INPETBEACH'.

Parentage:

*Female, or seed, parent*.—Proprietary selection of *Petunia* X *hybrida* identified as code number pt18-4122-5, not patented.

*Male, or pollen, parent*.—*Petunia* X *hybrida* 'Kerversalm', disclosed in U.S. Plant Pat. No. 19,329.

Propagation:

*Type*.—Terminal vegetative cuttings.

*Time to initiate roots, summer*.—About 10 to 15 days at temperatures ranging from 20 C to 30 C.

*Time to initiate roots, winter*.—About 15 to 20 days at temperatures about ranging from 18 C to 22 C.

*Time to produce a rooted plant, summer*.—About 15 days at temperatures about 25 C.

*Time to produce a rooted plant, winter*.—About 20 days at temperatures ranging from 18 C to 20 C.

*Root description*.—Fine, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright to outwardly spreading and mounding plant habit; freely branching habit with about nine to ten primary lateral branches with secondary laterals developing potentially at every node, dense and bushy plant form; pinching enhances development of lateral branches; vigorous growth habit and rapid growth rate.

*Plant height*.—About 14 cm.

*Plant diameter* (*area of spread*).—About 27 cm.

*Lateral branches*.—Length: About 11 cm. Diameter: About 3 mm. Internode length: About 1.25 cm. Strength: Strong; flexible, not brittle. Aspect: Initially upright then outwardly spreading. Texture and luster: Densely pubescent; pubescence, fine; matte. Color, developing and developed: Close to 144A.

Leaf description:

*Arrangement*.—Alternate before flowering; opposite after flowers develop; leaves simple.

*Length*.—About 4.2 cm to 4.4 cm.

*Width*.—About 2.5 cm to 2.75 cm.

*Shape*.—Ovate.

*Apex*.—Acute.

*Base*.—Obtuse with cuneate tendencies.

*Margin*.—Entire, slightly undulate.

*Texture and luster, upper surface*.—Slightly pubescent, pubescence, minute; matte.

*Texture and luster, lower surface*.—Slightly pubescent, pubescence, minute; slightly glossy.

*Venation pattern*.—Pinnate, arcuate.

*Color*.—Developing and fully developed leaves, upper surface: Close to between 147A and 139A; venation, close to 146A. Developing and fully developed leaves, lower surface: More green than 146A; venation, close to 146A.

*Petioles*.—Length: About 4 mm to 6 mm. Diameter: About 3 mm to 4 mm. Strength: Strong, flexible. Texture and luster, upper and lower surfaces: Moderately pubescent; slightly glossy. Color, upper surface: Close to 146A. Color, lower surface: Close to 146B.

Flower description:

*Flower type and flowering habit*.—Single terminal and axillary salverform flowers; flowers face mostly upward to outwardly; freely flowering habit with about 40 to 50 developing flowers and open flowers per plant at one time.

*Natural flowering season*.—Long day responsive; long flowering period, plants flower from early spring until frost in the autumn, flowering continuous during this period; early flowering habit, plants begin flowering about six weeks after planting rooted young plants.

*Flower longevity on the plant*.—Depending on temperature, about one to two weeks; petals not persistent, and sepals, persistent.

*Fragrance*.—None detected.

*Flower buds, before showing petal color*.—Length: About 1 cm. Diameter: About 4 mm. Shape: Oblong, elongate. Texture and luster: Pubescent; matte. Color, developing sepals: Close to between 144A and 146A. Color, developing petals: Close to 144A.

*Flower diameter*.—Relatively large, about 5.75 cm to 6 cm.

*Flower depth* (*height*).—About 3.75 cm to 4 cm.

*Throat diameter*.—About 1.5 cm to 1.7 cm.

*Tube length*.—About 2.5 cm to 2.75 cm.

*Tube diameter, distally*.—About 1.6 cm to 1.7 cm.

*Tube diameter, proximally*.—About 3 mm to 4 mm.

*Petals*.—Quantity and arrangement: Five petals fused in a single salverform whorl. Petal lobe length (from throat): About 2.5 cm to 2.75 cm. Petal lobe width: About 2.8 cm to 3.2 cm. Petal lobe shape: Roughly spatulate. Petal lobe apex: Broadly obtuse. Petal lobe margin: Entire; moderately undulate. Petal lobe texture and luster, upper surface: Smooth, glabrous; velvety; matte. Petal lobe texture and luster, lower surface: Mostly smooth and glabrous with sparse pubescent along midvein; matte. Throat texture and luster: Smooth, glabrous; slightly glossy. Tube texture and luster: Moderately to densely pubescent; slightly glossy. Color: When opening, upper surface: Initially, close to N57A becoming closer to 55A with development. When opening, lower surface: Close to 62B to 62C. Fully opened, upper surface: Close to N57A to N57B becoming closer to 55A; midvein, close to 144B variably tinged with close to 55A and lateral venation, close to 55A to 55B; color becoming closer to 55A to 55B with subsequent development. Fully opened, lower surface: Close to 62B to 62C; midvein, close to 144A and lateral venation, close to 62B to 62C; color becoming closer to 62C with subsequent development. Flower throat (inside): Close to NN155D and proximally, variably tinged with close to 144A; venation, close to 144A. Flower tube (outside): Close to 144A to 144B; venation, close to 144A to 144B.

*Sepals*.—Quantity and arrangement: Five sepals fused in a single star-shaped whorl; sepals flaring outwardly. Calyx length: About 2 cm. Calyx diameter: About 7.5 mm. Length: About 2 cm. Width: About 4 mm. Shape: Linear. Apex: Acute. Margin: Entire. Texture and luster, upper and lower surfaces: Moderately pubescent; pubescence, fine; matte to slightly glossy. Color, upper and lower surfaces: Close to 146A.

*Peduncles*.—Length: About 1.5 cm to 1.7 cm. Width: About 2 mm to 2.5 mm. Strength: Moderately strong; wiry and flexible, not brittle. Angle: About 30 to 45 degrees from the stem axis. Texture and luster: Densely pubescent; matte to slightly glossy. Color: Close to 144A.

*Reproductive organs*.—Stamens: Quantity per flower: About five. Filament length: About 2 cm. Filament color: Close to 157C to 157D. Anther length: About 1 mm. Anther shape: Bi-lobed. Anther color: Close to 160A. Pollen amount: Scarce. Pollen color: Close to 160A. Pistils: Quantity per flower: One. Pistil length: About 1.75 cm. Style length: About 1.6 cm. Style color: Close to 144B to 144C. Stigma diameter: About 2 mm. Stigma shape: Round to oblong. Stigma color: Close to 143A. Ovary color: Close to 144A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have excellent garden performance and have been observed to tolerate rain, wind and temperatures ranging from about 1 C to about 35 C.

It is claimed:

1. A new and distinct *Petunia* plant named 'INPET-BEACH' as illustrated and described.

* * * * *